(12) United States Patent
Fernandes

(10) Patent No.: US 8,455,602 B2
(45) Date of Patent: Jun. 4, 2013

(54) SUPRAMOLECULAR FUNCTIONAL MATERIALS

(75) Inventor: Manuel Antonio Fernandes, Johannesburg (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 229 days.

(21) Appl. No.: 12/862,251

(22) Filed: Aug. 24, 2010

(65) Prior Publication Data

US 2011/0046335 A1 Feb. 24, 2011

Related U.S. Application Data

(60) Provisional application No. 61/275,090, filed on Aug. 24, 2009.

(51) Int. Cl.
*C08G 79/00* (2006.01)
*C07F 3/00* (2006.01)
*C07F 15/00* (2006.01)

(52) U.S. Cl.
USPC .............................. 528/9; 556/131; 556/147

(58) Field of Classification Search
USPC ....................................... 528/9; 556/131, 147
See application file for complete search history.

(56) References Cited

U.S. PATENT DOCUMENTS

| | | | | |
|---|---|---|---|---|
| 3,396,177 | A * | 8/1968 | Thornton et al. | 549/208 |
| 5,656,709 | A * | 8/1997 | Fukushima et al. | 528/9 |
| 6,340,730 | B1 * | 1/2002 | Murray et al. | 526/114 |
| 7,736,757 | B2 * | 6/2010 | Takeuchi et al. | 428/690 |
| 7,763,365 | B2 * | 7/2010 | Takeuchi et al. | 428/690 |
| 7,951,745 | B2 * | 5/2011 | Zhou et al. | 502/171 |
| 8,008,418 | B2 * | 8/2011 | Morishita et al. | 528/9 |
| 2004/0254312 | A1 * | 12/2004 | Mawson et al. | 526/90 |
| 2006/0289839 | A1 * | 12/2006 | Emmerson et al. | 252/500 |
| 2007/0281182 | A1 * | 12/2007 | Schulte et al. | 428/690 |
| 2009/0000474 | A1 * | 1/2009 | MacGillivray | 95/90 |
| 2009/0048414 | A1 * | 2/2009 | Schlueter et al. | 528/9 |
| 2009/0048415 | A1 * | 2/2009 | Buesing et al. | 528/9 |
| 2009/0062409 | A1 * | 3/2009 | Matzger et al. | 521/50 |
| 2009/0062436 | A1 * | 3/2009 | Breiner | 524/117 |
| 2009/0092560 | A1 * | 4/2009 | Bagchi | 424/48 |

(Continued)

OTHER PUBLICATIONS

Zelenak (Inorganic Chemistry Communications, 10, 2007, 27-32).*

(Continued)

*Primary Examiner* — Liam Heincer
(74) *Attorney, Agent, or Firm* — Hamilton, Brook, Smith & Reynolds, P.C.

(57) ABSTRACT

The field of this invention relates to supramolecular functional materials, particularly to coordination networks, more particularly to coordination polymers, more particularly to metal based one-dimensional coordination polymers. The metal based one-dimensional coordination polymers comprises a repeat unit $[L_1\text{-}M\text{-}L_2]_n$ where $L_1$ and $L_2$ are one of a plurality of carboxylate ligands and $L_1$ can be the same as $L_2$, M is a metal, particularly a transition metal, and n is an integer from 1 to infinity. The metal based one-dimensional coordination polymers display one or more physico-chemical properties giving at least one functionality to the supramolecular material. Furthermore, a method of forming the metal based one-dimensional coordination polymers is provided by a chemical reaction between said organic ligand and said metal where said method comprises at least one selectable chemical reaction condition from the group comprising: volume of reaction vessel, material composition of reaction vessel, temperature, pressure, humidity and gas defining an atmosphere inside reaction vessel.

4 Claims, 7 Drawing Sheets

U.S. PATENT DOCUMENTS

| | | | | |
|---|---|---|---|---|
| 2009/0173666 | A1* | 7/2009 | Zhou et al. | 208/112 |
| 2009/0242856 | A1* | 10/2009 | Leznoff et al. | 252/582 |
| 2010/0019669 | A1* | 1/2010 | Akino et al. | 313/504 |
| 2010/0247477 | A1* | 9/2010 | Rauwald et al. | 424/78.3 |
| 2010/0331506 | A1* | 12/2010 | Fortte et al. | 526/241 |
| 2011/0003959 | A1* | 1/2011 | Reek et al. | 528/9 |
| 2011/0124808 | A1* | 5/2011 | Akino et al. | 524/610 |

OTHER PUBLICATIONS

Gavrilenko et al. (Journal of the American Chemical Society, 2005, 127, 12246-12253).*

Liu et al.(Inorganic Chemistry, 2007, 46, 6299-6310).*

Kumagai et al. (J. Chem. Soc. Dalton Trans. 2002, 3442-3446).*

Ball, P., "Scandal of Crystal Design . . . ," *Nature*, 381:648-650, (1996).

Chen, CT., and Suslick, K.S., "One-Dimensional Coordination Polymers: Applications to Material Science," *Coordination Chemistry Reviews*, 128:293-322, (1993).

Ferey, G., "Hybrid Porous Solids: Past, Present, Future," *Chem. Soc. Rev.*, 37:191-214, (2008).

Gavezzotti, A., "Are Crystal Structures Predictable?" *Acc. Chem. Res.*, 27:309-314, (1994).

Harvey, M.D., et al., "Room-Temperature and Near-Room-Temperature Molecule-Based Magnets," *Inorganic Chemistry*, 47:5649-5655, (2008).

Jain, R., et al., "High-Temperature Metal-Organic Magnets," *Nature*, 445:291-294, (2007).

Janiak, C. I., "Engineering Coordination Polymers Towards Applications," *Dalton Trans.*, pp. 2781-2804, (2003).

Kitagawa, S., et al., "Functional Porous Coordination Polymers," *Angew. Chem. Int. Ed.*, 43:2334-2375, (2004).

Lehn, J.M,, "Supramolecular Chemistry," *Science*, 260:1762-1763, (1993).

Maddox, J., "Crystals From First Principles," *Nature*, 335: p. 201, (1988).

Marais, C.G. "Thermodynamics and Kinetics of Sorption," Unpublished Master's Thesis, Stellenbosch University (2008).

Miller, J.S., "Design, Synthesis, and Characterization of Molecule-Based Magnets," In *Engineering of Crystalline Materials Properties*. Eds., JJ. Novoa, D. Braga and L. Addadi. Springer Science & Business Media B.V., Dordrecht, The Netherlands, pp. 291-306.

Gavrilenko, Konstantin S. et al., Delicate Crystal Structure Changes Govern the Magnetic Properties of 1D Coordination Polymers Based on 3d Metal Carboxylates; Chem. Eur. J. 2008, 14, 2034-2043.

Gavrilenko, Konstantin S. et al., Synthesis, Structure, and Magnetism of Heterometallic Carboxylate Complexes $[Mn^{III}_2 M^{II}_4 O_2(PhCOO)_{10}(DMF)_4]$, $M=Mn^{II}$, $Co^{II}$, $Ni^{II}$; Inorg. Chem., 2005, 44, 5903-5910.

* cited by examiner

| Structure | I | II | III | IV | V |
|---|---|---|---|---|---|
| Formula | [Zn($C_{10}H_9O_3$)$_2$] | [Co($C_{10}H_9O_3$)$_2$] | [Co($C_6H_7O_2$)$_2$] | [Co($C_{11}H_7O_2$)$_2$($C_3H_7O$)] | [Co$_2$($C_{15}H_9O_2$)$_4$($C_3H_7O$)$_2$] |
| Crystal System | Trigonal | Monoclinic | Orthorhombic | Orthorhombic | Monoclinic |
| Space Group | $P3_1$ | $P2_1/c$ | $Pbcn$ | $Pna2_1$ | $P2_1$ |
| Centrosymmetric | No | Yes | Yes | No | No |
| a/Å | 12.835(5) | 13.5904(3) | 17.4404(10) | 9.0360(2) | 25.1177(15) |
| b/Å | 12.835(5) | 9.6549(2) | 16.0775(11) | 22.4942(5) | 8.5110(5) |
| c/Å | 9.762(5) | 28.4950(6) | 10.4807(7) | 30.4984(7) | 25.7491(16) |
| α/° | 90 | 90 | 90 | 90 | 90 |
| β/° | 90 | 101.218(1) | 90 | 90 | 92.684(3) |
| γ/° | 120 | 90 | 90 | 90 | 90 |
| Volume/Å$^3$ | 1392.7(10) | 3667.51(14) | 2938.8(3) | 6199.0(2) | 5498.5(6) |
| Z | 1 | 4 | 8 | 4 | 4 |
| M---M contact distances | 3.469 | 3.169 | 3.143 | 3.224 | 3.482 |
| | - | 3.199 | - | 3.470 | 5.169 |
| | - | - | - | 3.475 | - |

FIG. 7

SUPRAMOLECULAR FUNCTIONAL MATERIALS

RELATED APPLICATIONS

This application claims the benefit of U.S. Provisional Application No. 61/275,090, filed on Aug. 24, 2009.

The entire teachings of the above application(s) are incorporated herein by reference.

FIELD OF THE INVENTION

This invention relates to supramolecular functional materials, particularly to coordination networks, more particularly to coordination polymers, and more particularly to metal based one-dimensional coordination polymers.

BACKGROUND OF THE INVENTION

Supramolecular chemistry is a relatively young branch of chemistry having undergone much of its development in the latter half of the 20th century [1]. The reason for this is twofold, firstly a thorough understanding of synthetic methods resulting in supramolecular systems was needed and secondly, powerful analytical technology used in structure elucidation and in physico-chemical property determination needed to be developed [1]. Analytical techniques that have been successfully employed in this regard include UV-visible, florescence-, and infra-red spectroscopy, nuclear magnetic resonance, powder X-ray diffraction and most importantly single-crystal X-ray diffraction [1]. Subsequently, the interest in supramolecular chemistry and the understanding of and rational design of property specific materials has increased over the last fifty years making supramolecular chemistry one of the fastest growing and most interdisciplinary areas in chemistry [1, 2, 3]. The quest to be able to manipulate and predict the nature of intermolecular forces in the design of property specific supramolecular entities remains one of the greatest scientific challenges of our day [1, 4, 5, 6].

One of the most studied areas at the moment is the formation of novel metal-organic frameworks (MOF's) and coordination polymers due to the possibility of using metal ions to align molecules in a desired direction [3, 7, 8]. One-dimensional (1D) coordination polymers have been extensively researched and subject to many review articles. It has been envisaged that these supramolecular materials could be used as molecular ferromagnets, metallic and superconducting polymers, non-linear optical materials and ferroelectric materials [9]. In more recent times the research focus has been aimed at magnetism and in particular room-temperature and near-room temperature molecular magnets [10-12]. The close packing of metal ions in a one-dimensional coordination polymer is favoured for the formation of functional materials characterized by displaying at least one physico-chemical property known to the group comprising: molecular ferromagnets, metallic and superconducting polymers, non-linear optical materials, ferroelectric materials and molecular magnets.

One of the chief problems encountered in this area of research is finding reliable methods for producing materials with interesting and possibly useful properties. Additionally, new materials showing promising physico-chemical properties are often extremely difficult to characterize and the exact formula and/or crystal structure of many of these materials remains unknown. Methods of ensuring successful single-crystal formation suitable for single-crystal X-ray diffraction need to be developed.

REFERENCES

1. Marais, C. G. (2008). *The thermodynamics and kinetics of sorption*. M. Sc thesis. University of Stellenbosch, South Africa.
2. Lehn, J-M. (1993). *Science,* 260, 1762.
3. Kitagawa, S., Kitaura, R., & Noro, S-I. (2004). *Angew. Chem. Int. Ed.,* 43, 2334.
4. Ball, P. (1996). *Nature,* 381, 648.
5. Maddox, J. (1988). *Nature,* 335.
6. Gavezzotii, A. (1994). *Acc. Chem. Res.,* 27, 309.
7. Ferey, G. (2008). *Chem. Soc. Rev.,* 37, 191.
8. Janiak, C. (2003). *Dalton Trans.,* 2781.
9. Chen, C-T., Suslick, K. S., (1993). *Coord. Chem. Rev.,* 128, 293.
10. Jain, R., Kabir, K., Gilroy, J. B., Mitchell, K. A. R., Wong, K-C., Hicks, R. G. (2007). *Nature,* 445, 291.
11. Harvey, M. D., Crawford, T. D., Yee, G. T. (2008). *Inorg. Chem.,* 47, 5649.
12. Miller, J. S. (2008) In *Engineering of Crystalline Materials Properties* (ed J. J. Novoa, D. Braga and L. Addadi), Springer Science & Business Media B. V., Dordrecht, The Netherlands, pp. 291-306.

The relevant teachings of the above references are incorporated herein by reference.

OBJECT OF INVENTION

It is an object of this invention to provide novel supramolecular functional materials comprising metal-based one-dimensional coordination polymers and at least one reliable method for their formation to at least alleviate the current disadvantage found in the current state of the art.

SUMMARY OF THE INVENTION

In accordance with this invention there is provided at least one supramolecular functional material comprising at least one, one-dimensional, metal-based coordination network.

There is further provided for the, or each, metal-based coordination network to be a metal-based one-dimensional coordination polymer, preferably comprising at least one organic ligand and at least one metal ion.

There is also provided for the metal-based coordination polymer to include at least one solvent molecule.

There is also provided for the metal ion and the organic ligand to form a chain structure when coordinated to one another to form the metal-based one-dimensional coordination polymer.

There is also provided for the metal ion, the organic ligand and the solvent molecule to form a chain structure and, thus form the metal-based one-dimensional coordination polymer.

There is also provided for the organic ligand to act, in use, as a bridging group between the metal ion forming the chain structure, for the organic ligand to be a carboxylate ligand.

There is also provided for the metal ion to be a transition group element, preferably selected from the group consisting of: titanium, vanadium, chromium, manganese, iron, cobalt, nickel, copper, zinc and cadmium.

There also provided for the metal-based coordination polymer to exhibit, in use, magnetic, electronic and/or optical physico-chemical properties.

The invention extends to a method of producing at least one supramolecular functional material comprising at least one metal-based coordination network, preferably a one-dimensional metal-based coordination network, alternatively a two-dimensional metal-based coordination network, further alternatively a three dimensional metal-based coordination network.

There is also provided for the method of producing the, or each, metal-based coordination network to be a metal-based one-dimensional coordination polymer, preferably comprising at least one organic ligand and at least one metal ion.

There is also provided for the method to include, in use, at least one solvent molecule.

There is also provided for the method wherein the metal ion and the organic ligand forms a chain structure when coordinated to one another forming the metal-based one-dimensional coordination polymer.

There is also provided for the method wherein the metal ion, the organic ligand and the solvent molecule forms a chain structure and, thus forming the metal-based one-dimensional coordination polymer, alternatively a two-dimensional coordination polymer, further alternatively a three-dimensional coordination polymer.

There is also provided for the method wherein the organic ligand acts, in use, as a bridging group between the metal ions forming the chain structure, for the organic ligand to be a carboxylate ligand.

There is also provided for the method wherein the metal ion is a transition group element, preferably selected from the group consisting of: titanium, vanadium, chromium, manganese, iron, cobalt, nickel, copper, zinc and cadmium.

There also provided the method wherein the metal-based coordination polymer to exhibit, in use, magnetic, electronic and/or optical physico-chemical properties.

There also provided the method wherein at least one reaction condition is selectable from a group consisting of: volume of reaction vessel, material composition of reaction vessel, temperature, pressure, humidity and gas defining an atmosphere inside reaction vessel.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1a shows the ligand-metal-ligand repeat unit forming the metal-based one-dimensional coordination polymer of the chemical formula $[Zn(C_{10}H_9O_3)_2]_n$;

FIG. 1b shows the coordination environment as a sequence of tetrahedra forming the metal-based one-dimensional coordination polymer of the chemical formula $[Zn(C_{10}H_9O_3)_2]_n$;

FIG. 1c a ball and stick representation of the crystal structure of the metal-based one-dimensional coordination polymer of the chemical formula $[Zn(C_{10}H_9O_3)_2]_n$ highlighting the coordination bonds between the ligand and metal ion;

FIG. 1d a packing diagram of the crystal structure of [Zn$(C_{10}H_9O_3)_2]_n$ as viewed down the crystallographic c-axis;

FIG. 2a shows the ligand-metal-ligand repeat unit fanning the metal-based one-dimensional coordination polymer of the chemical formula $[Co(C_{10}H_9O_3)_2]_n$;

FIG. 2b shows the coordination environment as a sequence of polyhedra forming the metal-based one-dimensional coordination polymer of the chemical formula $[Co(C_{10}H_9O_3)_2]_n$;

FIG. 2c a ball and stick representation of the crystal structure of the metal-based one-dimensional coordination polymer of the chemical formula $[Co(C_{10}H_9O_3)_2]_n$ highlighting the coordination bonds between the ligand and metal ion;

FIG. 2d a packing diagram of the crystal structure of [Co$(C_{10}H_9O_3)_2]_n$ as viewed down the crystallographic b-axis;

FIG. 3a shows the ligand-metal-ligand repeat unit forming the metal-based one-dimensional coordination polymer of the chemical formula $[Co(C_8H_7O_2)_2]_n$;

FIG. 3b shows the coordination environment as a sequence of polyhedra forming the metal-based one-dimensional coordination polymer of the chemical formula $[Co(C_8H_7O_2)_2]_n$;

FIG. 3c a ball and stick representation of the crystal structure of the metal-based one-dimensional coordination polymer of the chemical formula $[Co(C_8H_7O_2)_2]_n$ highlighting the coordination bonds between the ligand and metal ion;

FIG. 3d a packing diagram of the crystal structure of [Co$(C_8H_7O_2)_2]_n$ as viewed down the crystallographic c-axis;

FIG. 4a shows the ligand-metal-ligand repeat unit forming the metal-based one-dimensional coordination polymer of the chemical formula $[Co(C_{11}H_7O_2)_2(C_3H_7O)]_n$;

FIG. 4b shows the coordination environment as a sequence of polyhedra forming the metal-based one-dimensional coordination polymer of the chemical formula [Co $(C_{11}H_7O_2)_2(C_3H_7O)]_n$;

FIG. 4c a ball and stick representation of the crystal structure of the metal-based one-dimensional coordination polymer of the chemical formula $[Co(C_{11}H_7O_2)_2(C_3H_7O)]_n$ highlighting the coordination bonds between the ligand and metal ion;

FIG. 4d a packing diagram of the crystal structure of [Co $(C_{11}H_7O_2)_2(C_3H_7O)]_n$ as viewed down the crystallographic a-axis;

FIG. 5a shows the ligand-metal-ligand repeat unit forming the metal-based one-dimensional coordination polymer of the chemical formula $[Co(C_{15}H_9O_2)_4(C_3H_7O)_2]_n$;

FIG. 5b shows the coordination environment as a sequence of polyhedra forming the metal-based one-dimensional coordination polymer of the chemical formula $[Co(C_{15}H_9O_2)_4(C_3H_7O)_2]_n$;

FIG. 5c a ball and stick representation of the crystal structure of the metal-based one-dimensional coordination polymer of the chemical formula $[Co(C_{15}H_9O_2)_4(C_3H_7O)_2]_n$ highlighting the coordination bonds between the ligand and metal ion;

FIG. 5d a packing diagram of the crystal structure of [Co $(C_{15}H_9O_2)_4(C_3H_7O)]_n$ as viewed down the crystallographic b-axis;

FIG. 7 shows the crystallographic data for structures I to V.

DETAILED DESCRIPTION OF THE INVENTION

A description of example embodiments of the invention follows.

The teachings of all patents, published applications and references cited herein are incorporated by reference in their entirety.

While this invention has been particularly shown and described with references to example embodiments thereof, it will be understood by those skilled in the art that various changes in faun and details may be made therein without departing from the scope of the invention encompassed by the appended claims.

Figure 1:
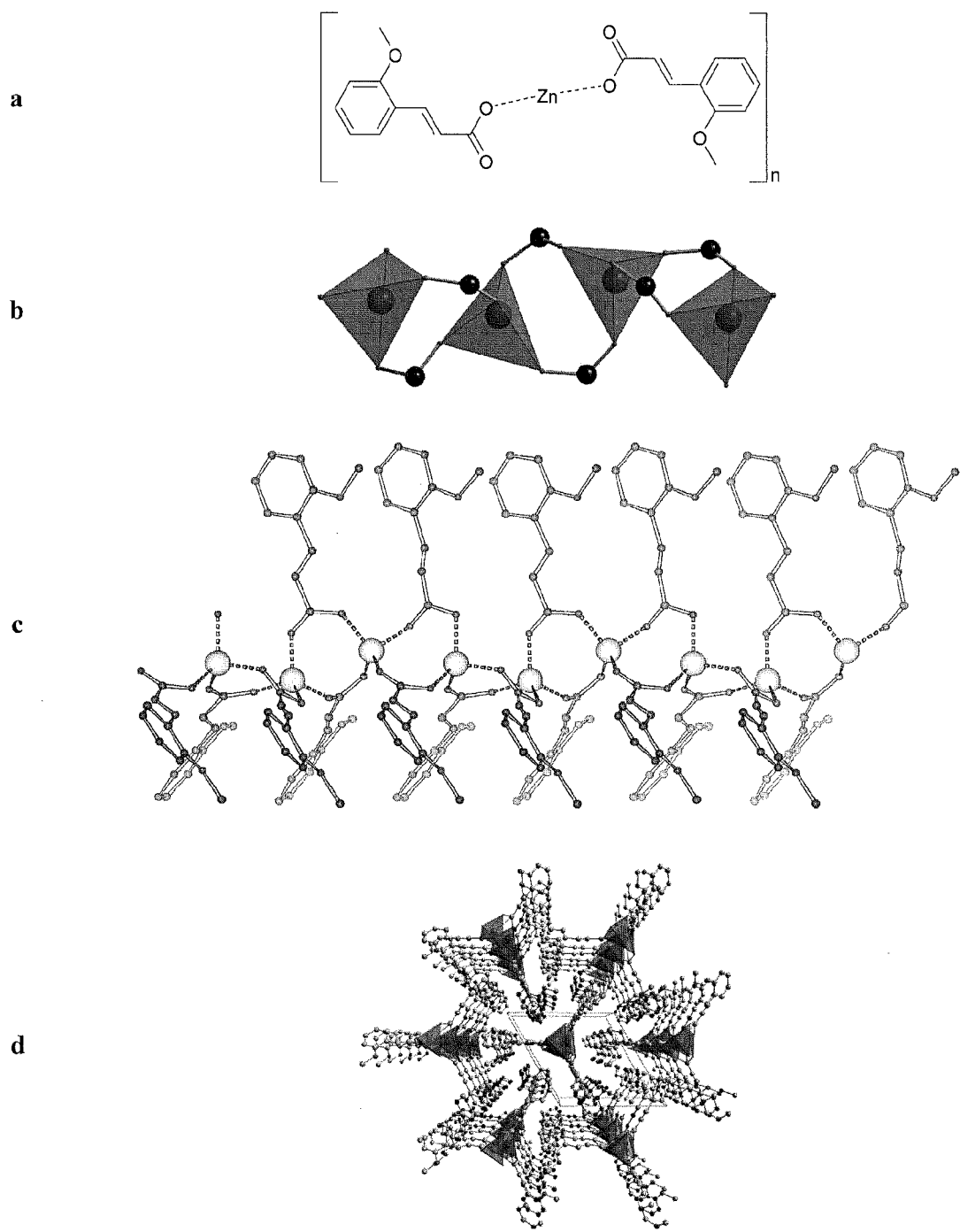
FIG. 1a-1d shows diagrams and schemes relating to structure I.

Referring to the drawings, (1a) to (1d) shows structure I of chemical formula $[Zn(C_{10}H_9O_3)2])_n$. FIG. (1a) shows the ligand-metal-ligand repeat unit $[L_1\text{-M-}L_2]_n$ forming a metal-based one-dimensional coordination polymer of the chemical formula $[Zn(C_{10}H_9O_3)_2]_n$ where n is any integer 1 to infinity, the metal is $Zn^{2+}$ and the ligand ($L_1$ and $L_2$) is o-methoxy-cinnamate. Coordination bonds formed between oxygen atoms of the carboxylate group comprising the ligand (o-methoxy-cinnamate) and the metal (zinc) ion are indicated by broken lines. The coordination environment of the metal-based one-dimensional coordination polymer of the chemical formula $[Zn(C_{10}H_9O_3)_2]_n$ is shown in (1b) as a sequence of polyhedra wherein the polyhedra are all tetrahedral. FIG. (1c) shows a ball and stick representation of the crystal structure of the metal-based one-dimensional coordination polymer of the chemical formula $[Zn(C_{10}H_9O_3)_2]_n$ highlighting the coordination bonds between the ligand and metal ion. The distance between zinc ions (Zn—Zn) comprising the metal-based one-dimensional coordination polymer was measured as 3.469 Å. FIG. 1d) shows a packing diagram of the crystal structure of $[Zn(C_{10}H_9O_3)_2]$ as viewed down the crystallographic c-axis. This is considered to be a very unusual structure as the ligands (o-methoxy-cinnamate) are arranged around the $Zn^{2+}$ in a propeller like $3_1$ screw axis arrangement resulting in a chiral structure crystallised in the chiral space group $P3_1$. There is provided that metal-based one-dimensional coordination polymer of the chemical formula $[Zn(C_{10}H_9O_3)_2]_n$ where n is any integer 1 to infinity, the metal is $Zn^{2+}$ and the ligand is o-methoxy-cinnamate may crystallize in other space groups and comprise polymorphs of the $P3_1$ structure. Crystallisation of $[Zn(C_{10}H_9O_3)_2]$ was achieved by heating a solution containing zinc metal and o-methoxy-cinnamatic acid at about 80° C. for about one week.

Figure 2:
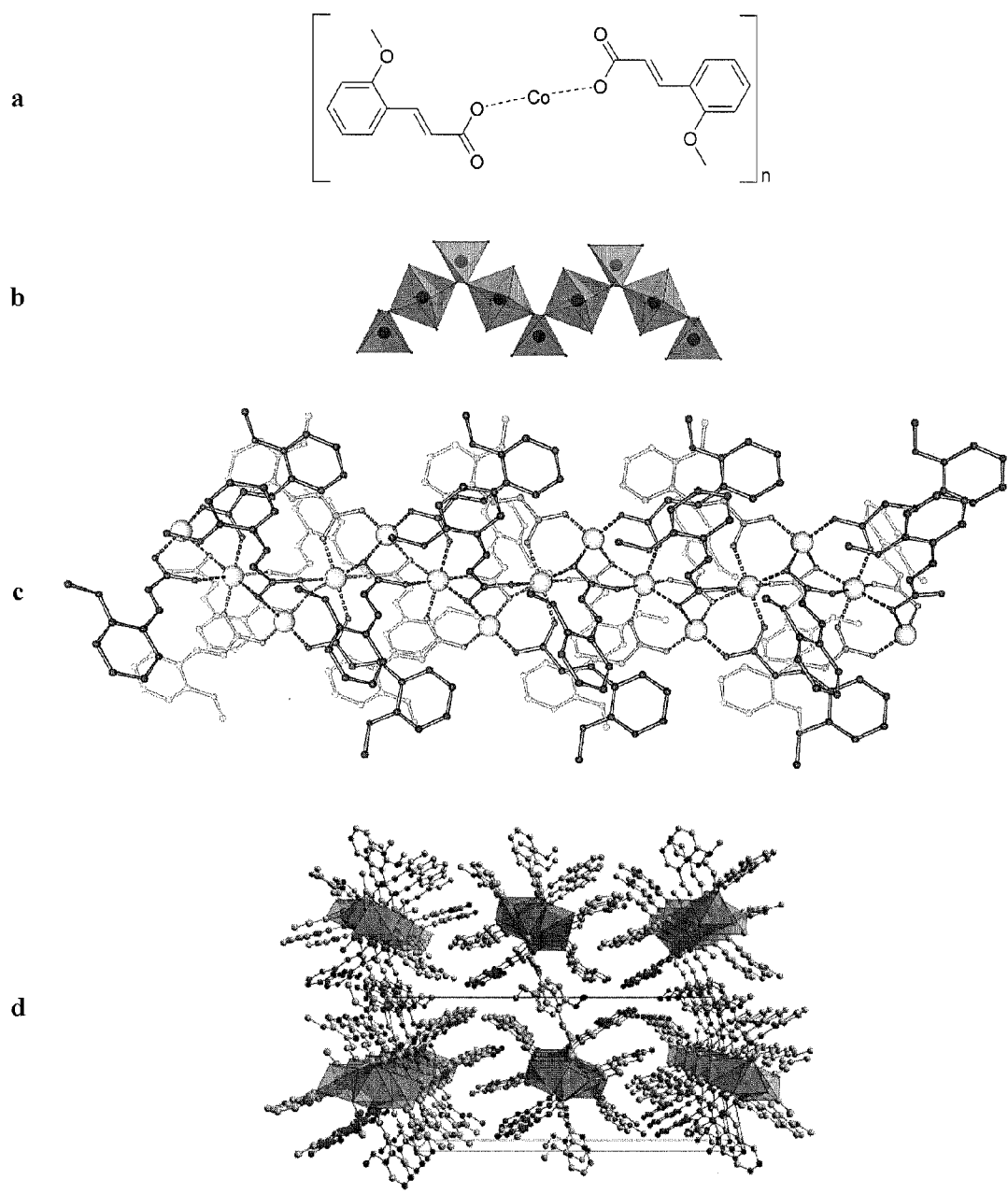
FIG. 2a-2d shows diagrams and schemes relating to structure II.

FIGS. (2a) to (2d) shows structure II of chemical formula $[Co(C_{10}H_9O_3)_2]_n$. FIG. 2a shows the ligand-metal-ligand repeat unit forming the metal-based one-dimensional coordination polymer of the chemical formula $[Co(C_{10}H_9O_3)_2]_n$ where n is any integer 1 to infinity, the metal is $Co^{2+}$ and the ligand is o-methoxy-cinnamate. Coordination bonds formed between oxygen atoms of the carboxylate group comprising the ligand (o-methoxy-cinnamate) and the metal (cobalt) ion are indicated by broken lines. The coordination environment of the metal-based one-dimensional coordination polymer of the chemical formula $[Co(C_{10}H_9O_3)_2]_n$ is shown in (2b) as a sequence of polyhedral wherein the polyhedra are an alternating sequence of corner sharing tetrahedra and octahedra. FIG. 2c) shows a ball and stick representation of the crystal structure of the metal-based one-dimensional coordination polymer of the chemical formula $[Co(C_{10}H_9O_3)_2]$ highlighting the coordination bonds between the ligand and metal ion.

The distance between cobalt ions (Co—Co) comprising the metal-based one-dimensional coordination polymer was measured as 3.169 Å and 3.199 Å. One of the interesting features of this crystal structure is that the arrangement of molecules around the cobalt ions causes the cobalt ions to be extremely close to one another along the chain comprising the metal-based one-dimensional coordination polymer. It is this distance which facilitates magnetic, electronic and/or optical physico-chemical properties or any combination of said physico-chemical properties characteristic of the metal-based one-dimensional coordination polymer of the chemical formula $[Co(C_{10}H_9O_3)_2]$. FIG. 2d) shows a packing diagram of the crystal structure of $[Co(C_{10}H_9O_3)_2]$ as viewed down the crystallographic b-axis. The crystal structure crystallises in the monoclinic, centrosymmetric space group $P2_1/c$. There is provided that metal-based one-dimensional coordination polymer of the chemical formula $[Co(C_{10}H_9O_3)_2]$ where n is any integer 1 to infinity, the metal is $Co^{2+}$ and the ligand is o-methoxy-cinnamate may crystallise in other space groups and comprise polymorphs of the $P2_1/c$ structure.

Figure 3:
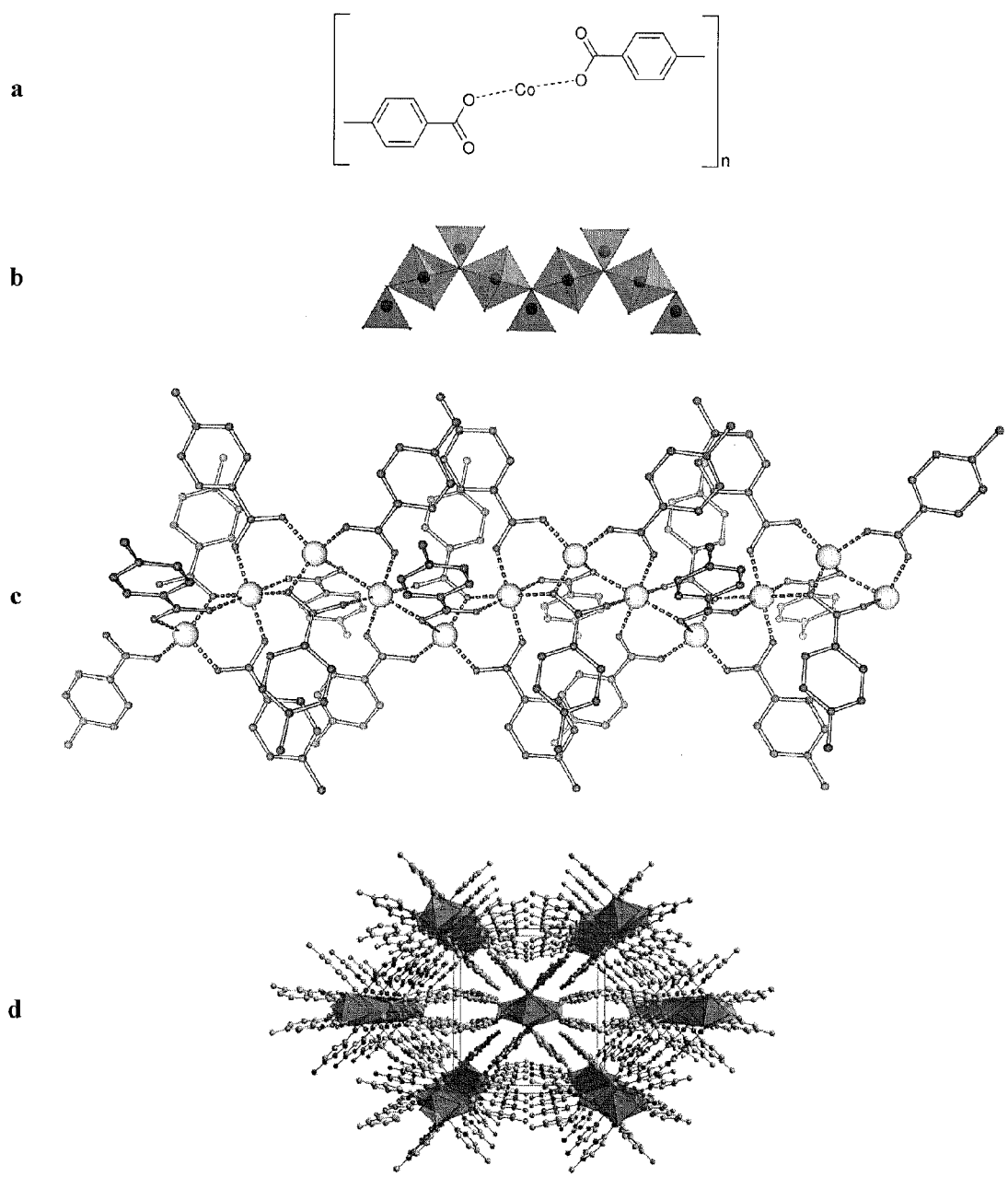
FIG. 3a-3d shows diagrams and schemes relating to structure III.

FIGS. (3a) to (3d) shows structure III of chemical formula $[Co(C_8H_7O_2)_2]_n$. FIG. 3a) shows the ligand-metal-ligand repeat unit forming the metal-based one-dimensional coordination polymer of the chemical formula $[Co(C_8H_7O_2)_2]_n$ where n is any integer 1 to infinity, the metal is $Co^{2+}$ and the ligand is p-toluate. Coordination bonds formed between oxygen atoms of the carboxylate group comprising the ligand (p-toluate) and the metal (cobalt) ion are indicated by broken lines. The coordination environment of the metal-based one-dimensional coordination polymer of the chemical formula $[Co(C_8H_7O_2)_2]_n$ is shown in (3b) as a sequence of polyhedra wherein the polyhedra are an alternating sequence of corner sharing tetrahedra and octahedra. FIG. 3c) shows a ball and stick representation of the crystal structure of the metal-based one-dimensional coordination polymer of the chemical formula $[Co(C_8H_7O_2)_2]_n$ highlighting the coordination bonds between the ligand and metal ion. The distance between cobalt ions (Co—Co) comprising the metal-based one-dimensional coordination polymer was measured as 3.143 Å. One of the interesting features of this crystal structure is that the arrangement of molecules around the cobalt ions causes the cobalt ions to be extremely close to one another along the chain comprising the metal-based one-dimensional coordination polymer. It is this distance which facilitates magnetic, electronic and/or optical physico-chemical properties or any combination of said physico-chemical properties characteristic of the metal-based one-dimensional coordination polymer of the chemical formula $[Co(C_8H_7O_2)_2]_n$. FIG. (3d) shows a packing diagram of the crystal structure of $[Co(C_8H_7O_2)_2]_n$ as viewed down the crystallographic c-axis. The crystal structure crystallises in the orthorhombic, centrosymmetric space group Pbcn. There is provided that metal-based one-dimensional coordination polymer of the chemical formula $[Co(C_8H_7O_2)_2]_n$ where n is any integer 1 to infinity, the metal is $Co^{2+}$ and the ligand is p-toluate may crystallise in other space groups and comprise polymorphs of the Pbcn structure.

Figure 4:
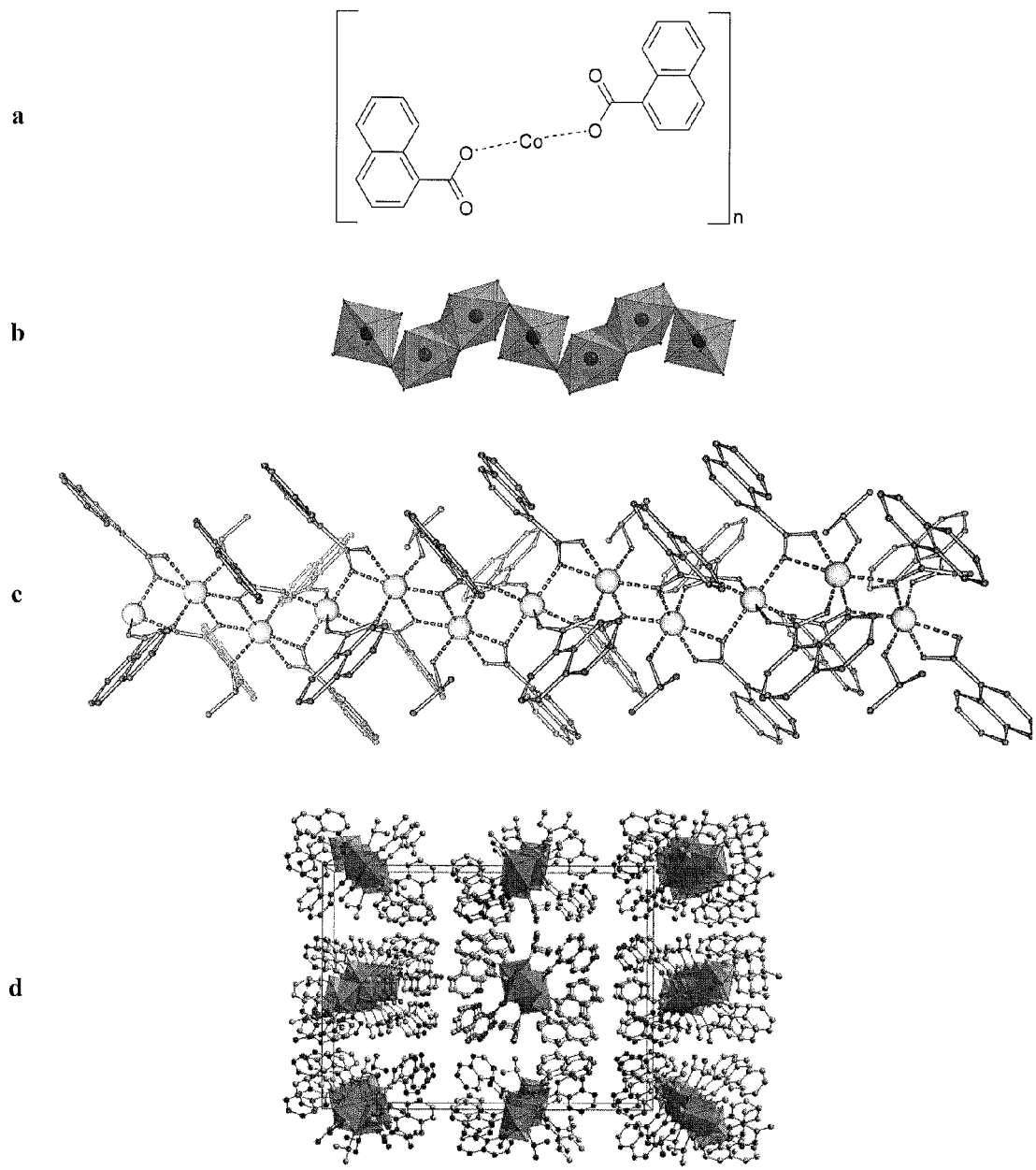
FIG. 4a-4d shows diagrams and schemes relating to structure IV.

FIGS. (4a) to (4d) shows structure IV of chemical formula $[Co(C_{11}H_7O_2)_2(C_3H_7O)]_n$. FIG. (4a) shows the ligand-metal-ligand repeat unit forming the metal-based one-dimensional coordination polymer of the chemical formula $[Co(C_{11}H_7O_2)_2(C_3H_7O)]_n$ where n is any integer 1 to infinity, the metal is $Co^{2+}$ and the ligand is naphthalene-1-carboxylic acid. Coordination bonds formed between oxygen atoms of the carboxylate group comprising the ligand (naphthalene-1-carboxylic acid) and the metal (cobalt) ion are indicated by broken lines. The coordination environment of the metal-based one-dimensional coordination polymer of the chemical formula $[Co(C_{11}H_7O_2)_2(C_3H_7O)]_n$, where n is shown in (4b) as a sequence of polyhedra wherein the polyhedra are an alternating sequence of corner sharing tetrahedra and octahedra. FIG. 4c) shows a ball and stick representation of the crystal structure of the metal-based one-dimensional coordination polymer of the chemical formula $[Co(C_{11}H_7O_2)_2(C_3H_7O)]_n$ highlighting the coordination bonds between the ligand and metal ion and between the isopropanol solvent and the metal ion. The distance between cobalt ions (Co—Co) comprising the metal-based one-dimensional coordination polymer was measured as 3.224 Å, 3.470 Å and 3.475 Å. FIG. 4d) shows a packing diagram of the crystal structure of $[Co(C_{11}H_7O_2)_2(C_3H_7O)]_n$ as viewed down the crystallographic a-axis. The crystal structure crystallises in the orthorhombic, non-centrosymmetric space group $Pna2_1$. There is provided that metal-based one-dimensional coordination polymer of the chemical formula $[Co(C_{11}H_7O_2)_2(C_3H_7O)]_n$ where n is any integer 1 to infinity, the metal is $Co^{2+}$ and the ligand is naphthalene-1-carboxylic acid may crystallise in other space groups and comprise polymorphs of the structure $Pna2_1$.

Figure 5:
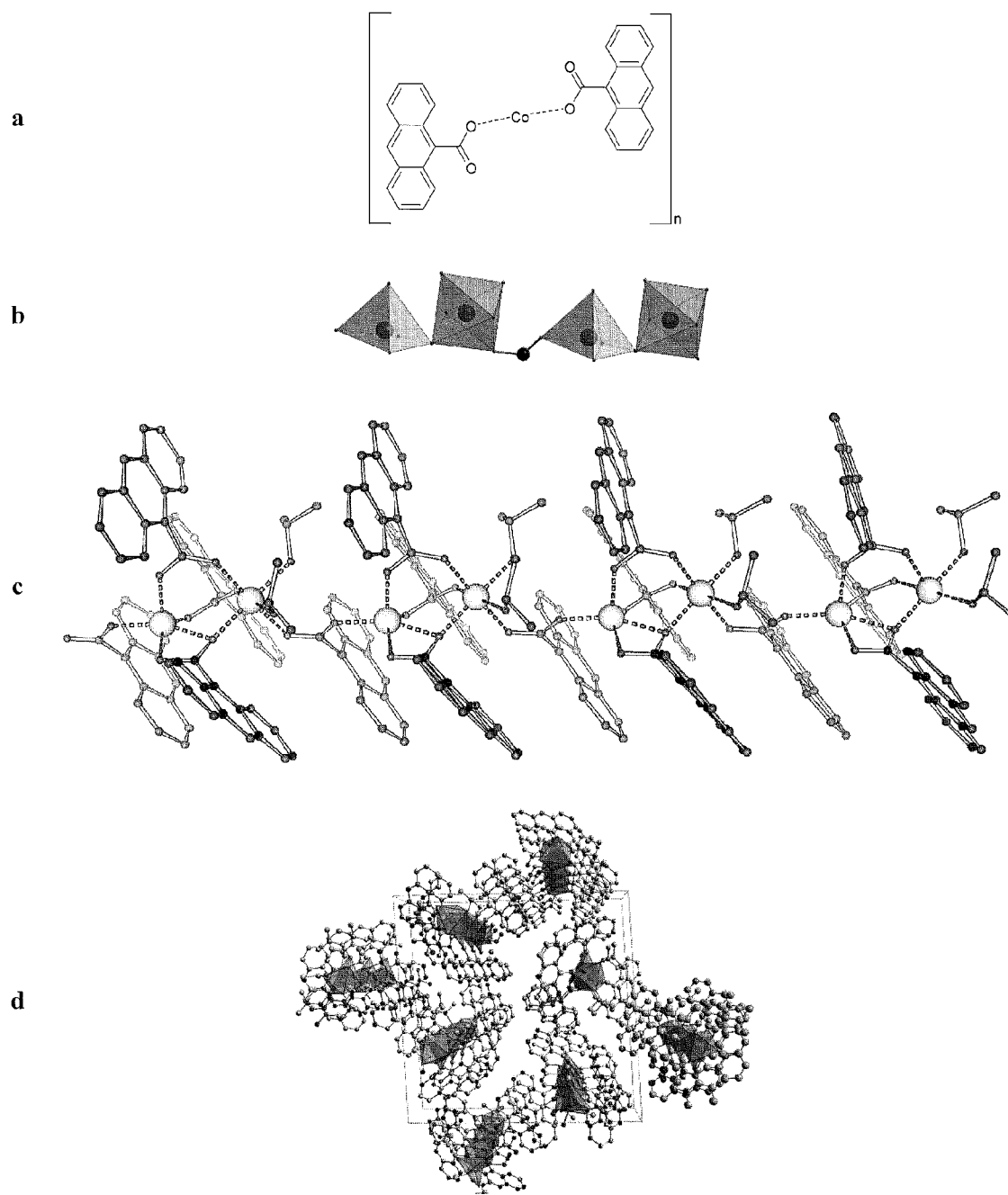
FIG. 5a-5d shows diagrams and schemes relating to structure V.

FIGS. (5a) to (5d) shows structure V of chemical formula $[Co(C_{15}H_9O_2)_4(C_3H_7O)_2]_n$. FIG. 5a) shows the ligand-metal-ligand repeat unit forming the metal-based one-dimensional coordination polymer of the chemical formula $[Co(C_{15}H_9O_2)_4(C_3H_7O)_2]_n$ where n is any integer 1 to infinity, the metal is $Co^{2+}$ and the ligand is anthracene-2-carboxylic acid. Coordination bonds formed between oxygen atoms of the carboxylate group comprising the ligand (anthracene-2-carboxylic acid) and the metal (cobalt) ion are indicated by broken lines. The coordination environment of the metal-based one-dimensional coordination polymer of the chemical formula $[Co(C_{15}H_9O_2)_4(C_3H_7O)_2]_n$ is shown in (5b) as a sequence of polyhedra wherein the polyhedra are an alternating sequence of edge sharing tetrahedra and octahedra. FIG. (5c) shows a ball and stick representation of the crystal structure of the metal-based one-dimensional coordination polymer of the chemical formula $[Co(C_{15}H_9O_2)_4(C_3H_7O)_2]_n$ highlighting the coordination bonds between the ligand and metal ion and between the isopropanol solvent and the metal ion. The distance between cobalt ions (Co—Co) comprising the metal-based one-dimensional coordination polymer was measured as 3.482 Å and 5.169 Å. FIG. (5d) shows a packing diagram of the crystal structure of $[Co(C_{15}H_9O_2)_4(C_3H_7O)_2]_n$ as viewed down the crystallographic b-axis. The crystal structure crystallises in the monoclinic, non-centrosymmetric space group $P2_1$. There is provided that metal-based one-dimensional coordination polymer of the chemical formula $[Co(C_{15}H_9O_2)_4(C_3H_7O)_2]_n$. where n is any integer 1 to infinity, the metal is $Co^{2+}$ and the ligand is anthracene-2-carboxylic acid may crystallize in other space groups and comprise polymorphs of the structure $P2_1$.

Figure 6:
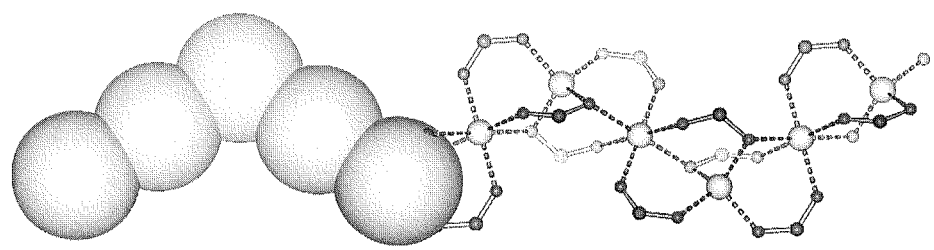
FIG. 6 shows the coordination environment of structure III partly in a space-filling representation and partly in a ball and stick representation.

FIG. 6 shows the coordination environment of structure III partly in a space-filling representation and partly in a ball and stick representation to indicate that the $Co^{2+}$ ions at closer than the sum of their van der Waals radii facilitating magnetic, electronic and/or optical physico-chemical properties or any combination of said physico-chemical properties characteristic of the metal-based one-dimensional coordination polymer herein described.

FIG. 7 shows the crystallographic data for structures I to V.

EXAMPLES

Embodiments of the invention will be illustrated by the following non-limiting examples of their synthesis and crystallisation. Several metal-based one-dimensional coordination polymers comprising zinc and cobalt metal ions and various aromatic carboxylates as ligands, have been crystallised via selective chemical reactive/interactive conditions.

The at least one supramolecular material comprising metal-based coordination networks in the form of metal-based one-dimensional coordination polymers are generally made via the direct reaction of the ligands (L) with the metal (M). The usual method of crystallisation is via reaction of a ligand (L) with a metal salt ($M^+$).

A typical non-limiting example of the crystallisation method used to form the supramolecular material of structure V is given.

0.2 g of anthracene-9-carboxylic acid and 0.027 g of Co metal (previously washed using 2M hydrochloric acid) were inserted into a Teflon hydrothermal bomb reactor. To this was added 10 ml of isopropanol. The reactor was then partially immersed in an oil bath and heated at 130° C. for 48 hours, followed by slow cooling to room temperature over 2 hours. The reaction product was then collected by filtration resulting in fine purple needle-like crystals (0.058 g). A single crystal of this was then selected and a single-crystal X-ray diffraction data set collected and solved. This structure, structure V, is presented in FIGS. (5a) to (5d).

Manganese supramolecular functional materials, as well as the zinc supramolecular functional materials described herein, were obtained by synthetic methods similar to those described in the preceding paragraph.

Not all structures employed the use of the Teflon hydrothermal bomb. For example structure I was crystallised by heating a solution containing zinc metal and o-methoxy-cinnamic acid at 80° C. for a week.

What is claimed is:

1. A supramolecular functional material of the chemical formula $[Zn(C_{10}H_9O_3)_2]_n$ crystallised in the space group $P3_1$ wherein n is any integer from 1 to infinity.

2. A supramolecular functional material of the chemical formula $[Co(C_{10}H_9O_3)_2]_n$ crystallised in the space group $P2_1/c$ wherein n is any integer from 1 to infinity.

3. A supramolecular functional material of the chemical formula $[Co(C_{11}H_7O_2)_2(C_3H_7O)]_n$ crystallised in the space group $Pna2_1$ wherein n is any integer from 1 to infinity.

4. A supramolecular functional material of the chemical formula $[Co(C_{15}H_9O_2)_4(C_3H_7O)_2]_n$ crystallised in the space group $P2_1$ wherein n is any integer from 1 to infinity.

* * * * *